United States Patent [19]

Najer et al.

[11] 4,001,251
[45] Jan. 4, 1977

[54] APOVINCALDEHYDE

[75] Inventors: Henry Najer; Yves Robert Alain Pascal, both of Paris, France

[73] Assignee: Synthelabo, Paris, France

[22] Filed: June 5, 1975

[21] Appl. No.: 583,893

Related U.S. Application Data

[62] Division of Ser. No. 423,901, Dec. 12, 1973, Pat. No. 3,925,392.

[30] Foreign Application Priority Data

Dec. 15, 1972 France .............................. 72.44673

[52] U.S. Cl. .......................................... 260/293.53
[51] Int. Cl.$^2$ ...................................... C07D 459/00
[58] Field of Search ............................... 260/293.53

[56] References Cited

OTHER PUBLICATIONS

Blaha et al., Collect. Czech. Chem. Commun. 1968, 33 (11), 3833–3847, C.A. 70: 29146h (1969).

*Primary Examiner*—G. Thomas Todd
*Attorney, Agent, or Firm*—Armstrong, Nikaido & Wegner

[57] ABSTRACT

Vincamine and/or its stereoisomers, a known drug, is made from vincaminol and/or its stereoisomers by successive conversion of the latter into apovincaldehyde, apovincamine, and 16-methoxycarbonyl-eburnane, followed by conversion of the last into vincamine either directly by introduction of a 16-hydroxyl group or by hydrolysis, introduction of a 16-hydroxyl group, and re-esterification.

1 Claim, No Drawings

APOVINCALDEHYDE

This is a division of application Ser. No. 423,901, filed Dec. 12, 1973, now U.S. Pat. No. 3,925,392.

The present invention provides a process for preparing vincamine and its stereoisomers from vincaminol, which is a known compound, the synthesis of which from indole has been described by Castedo, Harley-Masar and Leeney (Chem. Comms. 1968, 1186).

and introducing a hydroxyl radical at position 16 of this carbanion, to give vincamine, 16-epivincamine and/or their stereoisomers, or (B) saponifying the 16-methoxycarbonyl-eburnane stereoisomers to give 16-carboxyeburnanes, converting the latter into a carbanion, introducing a hydroxyl radical at position 16 of this anion, and esterifying the product to give vincamine, 16-epivincamine, and/or their stereoisomers.

The process of the invention may be represented by the following reaction scheme:

STEP I

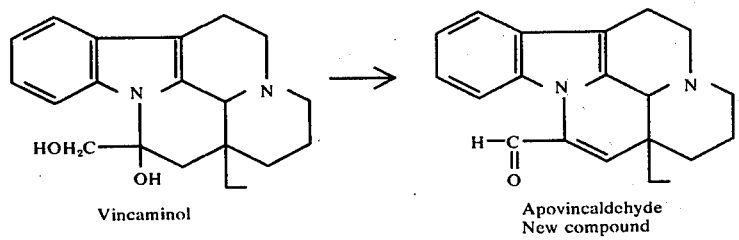

Vincaminol → Apovincaldehyde
New compound

STEP II

Apovincaldehyde →

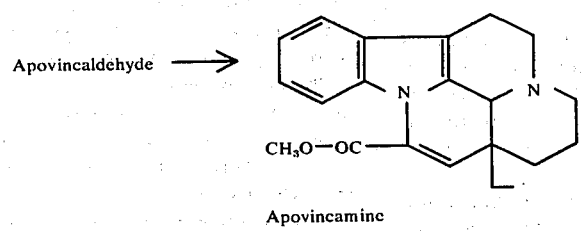

Apovincamine

STEP III

Apovincamine →

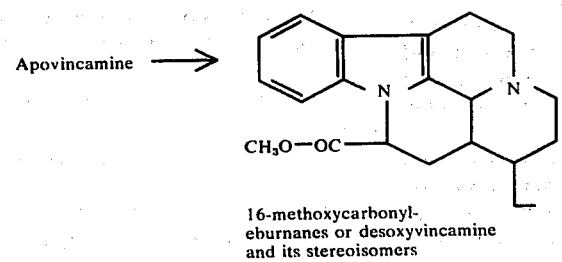

16-methoxycarbonyl-eburnanes or desoxyvincamine and its stereoisomers

STEP IV

Desoxyvincamine and its stereo-isomers →

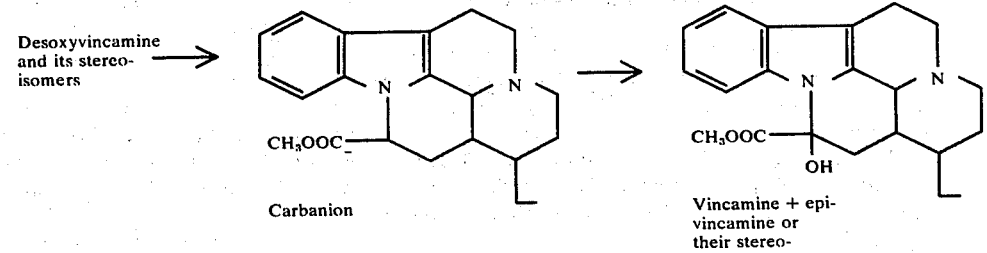

Carbanion → Vincamine + epi-vincamine or their stereo-isomers

The process of the invention comprises converting vincaminol and/or its stereoisomers into apovincaldehyde and/or its stereoisomers, converting the latter into apovincamine and/or its stereoisomers, hydrogenating apovincamine and/or its stereoisomers to give a mixture of 16-methoxycarbonyl-eburnane stereoisomers, and either (A) converting the latter into a carbanion In the variant of the process 16-methoxycarbonyleburnanes are saponified to 16-carboxy-eburnanes before the conversion to the carbanion and the attachment of the OH radical at position 16. The vincaminic and epivincaminic acids obtained are then esterified. This variant (step IV bis) may be represented as follows:

STEP IV BIS

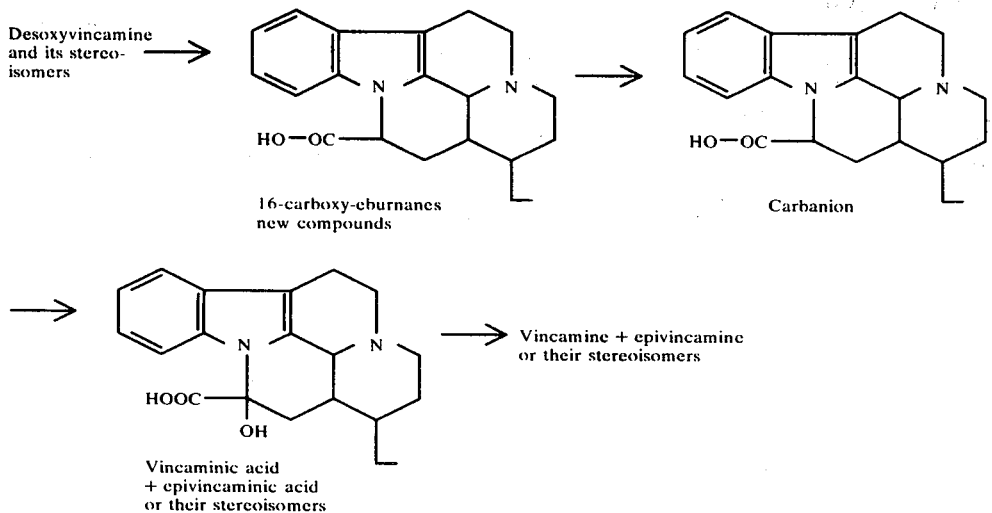

Vincamine alone may be obtained by adopting one of the following procedures:

I. The mixture of vincamine and epivincamine is treated under hot conditions with potassium hydroxide in an alcohol, for example methanol; this causes saponification with epimerisation, so that pure vincaminic acid is obtained. The latter can then be esterified to give vincamine.

II. In the preceding stage, the mixture of vincaminic and epivincaminic acids is epimerised by treatment with potassium hydroxide; pure vincaminic acid is then collected and esterified to give vincamine.

When epimerisation is not carried out, the proportion of vincamine in the mixture of vincamine and epivincamine is approximately 50%. If so desired, after separation, it is possible to recycle the epivincamine which is converted to apovincamine.

Step I is an oxidising dehydration preferably carried out with phosphorus pentoxide and dimethylsulphoxide, at a temperature from 0° to 150° C, in the presence or absence of a solvent and, advantageously, with addition of pyridine.

Step II, the conversion of an aldehyde to an ester, is preferably carried out by reacting the aldehyde with an alkali metal cyanide, dissolved in a hydroxyl-containing solvent such as an alcohol, followed by oxidation, in the presence of acetic acid, with, for example, manganese dioxide. This reaction is carried out at the laboratory temperature.

Step III, hydrogenation of apovincamine, has already been described, in particular by Trojanek and colleagues (Tet. Letters, 1961, 702) and by Clauder and colleagues (ibid. 1962, 1147).

The first part of step IV (conversion to the carbanion) may be carried out over a wide range of temperatures (-100° to +100° C) depending on the reagents used, in an aprotic solvent such as anhydrous tetrahydrofuran or hexamethylphosphorotriamide or a mixture of the two, by the action of a strong organic base such as triphenylmethyl sodium, or an alkali metal amide, for example lithium diisopropylamide or lithium cyclohexylisopropylamide.

The second part of this step is effected by the action of molecular oxygen, and can consist of simply bubbling air into the reaction mixture.

In step IV bis, the prior saponification of the ester to the acid takes place under conventional conditions, using an alkali metal hydroxide, under cold conditions, in an alcohol, followed by acidification. The conversion to the carbanion and the attachment of the OH radical at position 16 by reaction of a strong organic base and passage of oxygen, are similar to that described in step IV. However, the reaction is generally carried out at a temperature of 0° to +100° C.

The subsequent esterification of the acids obtained is well known; see especially Trojanek et al and Clauder et al (loc. cit.).

The conversion of epivincamine to apovincamine is carried out by the action of acetic anhydride or formic acid.

The following non-limiting Example illustrates the invention.

EXAMPLE

STEP I: Apovincaldehyde 10 ml of anhydrous pyridine followed by 5g of phosphorus pentoxide, added gradually in small amounts, are added to a solution of 5g (0.015mol) of vincaminol in 50 ml of dimethylsulphoxide. A spontaneous rise in temperature is observed. The mixture is then heated for 1 hour at 100° C, a further 10 ml of dimethylsulphoxide, 5 ml of pyridine and 5g of phosphorus pentoxide are added, followed again, after 2 hours, by 10 ml of pyridine and 5g of phosphorus pentoxide. The reaction is completed by adding a further 5g of phosphorus pentoxide after 1 hour, and by heating the reaction mixture for 3 hours at 100° C.

The mixture is left to cool, and excess potassium carbonate is added, followed by water, added dropwise. The mixture is extracted three times in succession with 50 ml of ether, the combined ether extracts are washed twice in succession with a saturated solution of sodium chloride, dried over sodium sulphate and filtered, and the solvent is driven from the filtrate on a water bath in vacuo.

The oily residue is chromatographed on alumina, eluting with benzene. In the eluate, after evaporation of the solvent, 3.7g (yield = 80%) of apovincaldehyde are collected in the form of an oil which, when redissolved in petroleum ether (35°–70° C) and precipitated by means of benzene, is in the form of a yellow crystalline compound, solvated with one molecule of benzene, which melts at 94° C.

Analysis: $C_{20}H_{22}N_2O$ (M.W. 306)

| | | | |
|---|---|---|---|
| Calculated | % C | 81.3 | H 7.34 |
| Found | % | 81.37 | 7.34 |

STEP II: Apovincamine 500 mg (0.0016 mol) of apovincaldehyde are dissolved in 10 ml of anhydrous methanol, and 820 mg (0.017 mol) of sodium cyanide and 300 mg (0.005 mol) of acetic acid are added, followed, after 10 minutes, by 5.75g (0.066 mol) of active manganese dioxide freshly prepared by the method of Corey, Gilman and Granem (J.Amer.Chem.Soc., 1968, 90, page 5615) and finely ground.

The mixture is left to stand overnight at ambient temperature. Excess sodium bicarbonate is added and the mixture is extracted three times in succession with ethyl acetate. The combined ethyl acetate extracts are washed in succession with 0.1 N sodium hydroxide solution and a saturated solution of sodium chloride; they are dried over sodium sulphate and filtered; the solvent is evaporated from the filtrate and apovincamine is crystallized by triturating the residual oil in diethyl ether. The ether is evaporated and the residue is triturated in petroleum ether (35°–70° C) and drained.

450 mg (yield = 82%) of apovincamine, m.p. 162° C, are thus collected; it is identified by its mixed melting point and its infra-red and NMR spectra, compared with an authentic sample.

STEP III: Desoxyvincamines 14.1g (0.042 mol) of apovincamine are dissolved in 250 ml of ethyl acetate, 2g of 5% palladium on charcoal are added and the mixture is hydrogenated over the course of 2 hours at 70° C under 100 atmospheres initial pressure. The mixture is allowed to cool, the catalyst is filtered off and washed with chloroform and the solvents are evaporated from the filtrate.

13g (yield = 92%) of a mixture of desoxyvincamines, which melts at 125°–130° C, are thus collected.

STEP IV: Vincamine and 16-epivincamine 3.4g (0.01 mol) of the mixture of desoxyvincamines are added to a solution of lithium cyclohexylisopropylamide in tetrahydrofuran, prepared beforehand from 1.4g (0.01 mol) of cyclohexylisopropylamine and 5 ml of a 2.14 N solution of butyl-lithium in diethyl ether, cooled to −78° C.

A stream of air is bubbled into this mixture, gradually allowing the temperature to return to that of the laboratory. After bubbling for 48 hours, a saturated solution of sodium bicarbonate is added. The mixture is extracted several times with methylene chloride, and the combined methylene chloride extracts are dried over sodium sulphate and filtered; the solvent is evaporated from the filtrate on a water bath in vacuo, the oily residue is triturated in diethyl ether and the precipitate consisting of a mixture of vincamine and 16-epivincamine is filtered off.

STEP IV BIS:

1. Desoxyvincaminic and 16-epidesoxyvincaminic acids

A suspension of 4g (0.012 mol) of the mixture of desoxyvincamines in a solution of 5g of potassium hydroxide in 50 ml of methyl alcohol is left to stand overnight, with stirring. Water is added, the pH is adjusted to 6.5 by adding 0.1 N hydrochloric acid, and the product is filtered off, washed with water and dried in vacuo over phosphorus pentoxide.

3.5g (yield = 91%) of a mixture of desoxyvincaminic and 16-epidesoxyvincaminic acids, which melts at a temperature above 250° C, are thus collected.

Analysis: $C_{20}H_{24}O_2N_2$ (M.W. = 324)

| | | | | |
|---|---|---|---|---|
| Calculated | % C 73.9 | | H 7.44 | N 8.65 |
| Found | % 73.57 | | 7.51 | 8.59 |

2. Vincaminic and 16-epivincaminic acids

A mixture of 1.25g (0.004 mol) of desoxyvincaminic and 16 epidesoxyvincaminic acids is added to a solution in anhydrous tetrahydrofuran of lithium diisopropylamide prepared at the time of use from 0.8g (0.008 mol) of diisopropylamine and 4 ml of a 2.1 N solution of butyl-lithium (0.0085 mol) in diethyl ether. The mixture is left to stand at 0° C for 30 minutes and is then heated at 50° C for 1 hour. It is cooled in an ice bath and a stream of air is bubbled into it for 6 hours. 10 ml of methanol and 10 ml of water are then added and the pH of the solution is adjusted to pH 7.5 by means of N hydrochloric acid. A precipitate consisting of a mixture of vincaminic and 16-epivincaminic acids is thus obtained and is filtered off and dried for 2 hours at 120° C over phosphorus pentoxide and under a residual vacuum of 20 mm.

1g (yield = 76%) of this mixture, which melts at a temperature above 250° C, is finally collected.

Analysis: $C_{20}H_{24}O_3N_2$ (M.W. = 340)

| | | | | |
|---|---|---|---|---|
| Calculated | % C 70.6 | H 7.10 | H 8.24 | O 14.15 |
| Found | % 70.4 | 7.13 | 8.30 | 13.9 |

3. Vincamine and 16-epivincamine

A solution of diazomethane in diethyl ether is added to a suspension of 1g (0.003 mol) of the mixture of vincaminic and 16-epivincaminic acids in methylene chloride, cooled to 0° C. The mixture is left to stand at ambient temperature for 2 hours and is acidified with acetic acid; the solvents are driven off on a water bath is vacuo and the residue is extracted with methylene chloride; the latter extract is washed in succession with a 0.1 N solution of sodium hydroxide and then with water, is dried over sodium sulphate and filtered; the solvent is evaporated on a water bath in vacuo.

The residue of 0.96g (yield = 92%) is chromatographed on 30g of alumina. By eluting first with benzene and then with chloroform, vincamine and 16-epivincamine are collected separately.

Epimerisation

A mixture of 200 mg (0.0006 mol) of vincamine and 16-epivincamine in 25 ml of methyl alcohol containing 200 mg (0.0036 mol) of potassium hydroxide is heated under reflux for 5 hours. The solvent is driven off and water is added, followed by 0.1 N hydrochloric acid until the pH is 6.5.

180 mg (yield = 94%) of vincaminic acid are thus collected and are converted to vincamine by reaction with diase methane.

Conversion of epivinicamine to apovincamine

A solution of 3.54g (0.01 mol) of 16-epivincamine in 50 ml of formic acid is heated under reflux for 10 hours, under nitrogen. The formic acid is evaporated on a water bath in vacuo, the residue is dissolved in methylene chloride, and the latter solution is washed with a saturated solution of sodium bicarbonate and with water. The solution is dried over sodium sulphate and filtered, and the methylene chloride is evaporated from the filtrate. 2.7g (yield = 80%) of apovincamine are thus collected.

We claim:
1. Apovincaldehyde of the formula:

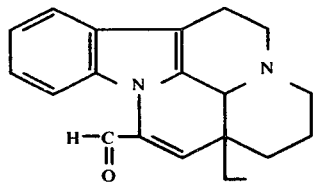

and its stereoisomers.